United States Patent [19]
Voorhees et al.

[11] Patent Number: 5,354,472
[45] Date of Patent: Oct. 11, 1994

[54] ANION EXCHANGE MATERIALS COMPRISED OF DERIVATIZED CELLULOSE-POLYESTER COMPOSITES

[75] Inventors: Marc Voorhees, Arvada; Ben F. Brian, III, Littleton; Lloyd Forrestal, Boulder, all of Colo.

[73] Assignee: Cobe Cardiovascular, Inc., Arvada, Colo.

[21] Appl. No.: 981,912

[22] Filed: Nov. 23, 1992

Related U.S. Application Data

[63] Continuation of Ser. No. 802,185, Dec. 4, 1991, abandoned.

[51] Int. Cl.$^5$ .......................... B01D 15/08; C02J 5/20
[52] U.S. Cl. .................... 210/635; 210/656; 424/78.1; 424/78.17; 521/28; 521/30; 521/27; 422/28
[58] Field of Search ............... 521/30, 28, 27; 424/78.1, 78.17; 422/28; 210/78.1, 635, 656

[56] References Cited

U.S. PATENT DOCUMENTS

| | | |
|---|---|---|
| 3,472,840 | 10/1969 | Stone et al. |
| 4,070,287 | 1/1978 | Wiegand et al. ................ 210/679 |
| 4,335,717 | 10/1982 | Antrim et al. ................... 521/32 |
| 4,663,163 | 5/1987 | Hou et al. ....................... 502/404 |
| 4,800,016 | 1/1989 | Yang .............................. 502/404 |
| 4,810,567 | 3/1989 | Calcaterra et al. ............. 424/78.17 |
| 5,151,192 | 9/1992 | Matkovich ..................... 210/646 |

FOREIGN PATENT DOCUMENTS

| | | |
|---|---|---|
| 0219053 | 4/1987 | European Pat. Off. |
| 55-129066 | 10/1980 | Japan ............................. 210/679 |
| 2080056 | of 1990 | Japan. |
| 0466178A1 | 1/1992 | PCT Int'l Appl. |
| 1601464 | 10/1981 | United Kingdom. |

OTHER PUBLICATIONS

IDE Sought for Heparin Removal Device, The BBI Newsletter, vol. 17, No. 3:56–57 (Mar. 1994).
Confidential Disclosure of Invention entitled "A Method for Producing Whole Blood Compatible Anion Exchange Materials", by Brian, Voorhees and Forrestal, dated Feb. 12, 1991.
Ito et al. (1986) Journal of Applied Polymer Science 31:2491–2500, entitled: Formation of polyelectrolyte . . .
Ben F. Brian, III, Ph.D. Thesis, 1991, entitled: Augmented hemoperfusion for hyperbilirubinemia.

*Primary Examiner*—G. S. Kishore
*Assistant Examiner*—Peter F. Kulkosky
*Attorney, Agent, or Firm*—Beaton & Swanson

[57] ABSTRACT

A novel biocompatible anion exchange membrane is prepared by reacting the hydroxyl groups of a chromatographic support material with a polyester-cellulose solution containing glycidyl trimethyl ammonium chloride and bis glycidyl polyethylene oxide.

25 Claims, 2 Drawing Sheets

ANION EXCHANGE MATERIALS COMPRISED OF DERIVATIZED CELLULOSE-POLYESTER COMPOSITES

This is a continuation of copending application Ser. No. 07/802,185 filed on DEc. 4, 1991, now abandoned.

FIELD OF INVENTION

This invention describes novel biocompatible anion exchange materials and methods for their production and use. In addition, this invention discloses methods of treatment of biological fluids such as whole blood for the selective removal of anionic species with the biocompatible anion exchange materials of the present invention.

BACKGROUND OF THE INVENTION

The scope of the present invention is broad, incorporating: novel anion exchange materials, novel support materials for affinity or ion chromatographic materials, methods for producing the anion exchange materials, methods for removing species from biological fluids such as whole blood, improved methods for processing blood extracorporeally and methods of medical treatment. In one embodiment of the invention there is disclosed an extracorporeal treatment process for removing heparin from whole blood by passing the heparin containing blood through a filter device containing the biocompatible anion exchange material of the present invention.

There are a wide number of applications where it is desirable to remove anionic (negatively charged) species or chemicals from whole blood. For example, anionic exchange materials—supports that have cationic or positively charged surfaces—have been suggested for the removal of barbiturates in drug overdose cases, bilirubin from jaundiced patients and heparin for the prevention of post-operative bleeding. See, e.g., Cipoletti, et al., Resin Technology in Medicine in *Sorbents and Their Clinical Applications*, Giordano ed., Academic Press, New York, 1980; Sideman et al., *Contr. Nephrol.*, 29:90-100, 1982; U.S. Pat. No. 4,800,016 of Yang; Matsuda et al., *Art Organs*, 13:504-7, 1989; Hov et al., *Art Organs.*, 14:436-442, 1990.

Supported cationic surfaces have also been suggested for the use of the removal of coagulation factors at polymer surfaces for reduced thrombogenicity and improved biocompatibility. See, Wilson, *Drug Dev. Res.*, 21:79-92, 1990.

Despite the promise of such techniques, the use of anionic exchange materials in whole blood applications has been limited by the biocompatability of the materials used. With the materials used to date, all researchers have noticed a demonstrable removal of platelets—and to a lesser extent white blood cells—from the whole blood samples passed over anion exchange supports. Previous attempts have been made to coat or shield the cation on the surface of the support materials in order to prevent the removal of blood components while retaining the ability to associate with anionic species in the whole blood sample. Such attempts have led to reductions in efficiency and/or capacity to remove anionic species from the whole blood. This is especially true where the anionic species that are being removed from the blood are relatively large (heparin, coagulation factors, etc.)

The use of the anionic exchange materials of the present invention need not be limited to the removal of anionic species. The biocompatible material can be further modified to yield chromatographic materials that rely on affinity interactions.

U.S. patent application Ser. No. 07/562,009 (the '009 Application) is commonly assigned with the present application. In the '009 Application, a method of medical treatment is described wherein a medical agent is administered to a patient, and after a period of time the medical agent is removed extracorporeally by passing body fluid over a support adopted to immobilize the agent. Several embodiments of the present invention are adaptable for use in the method described in the '009 Application due to the biocompatability of the anion exchange materials disclosed herein.

In one such embodiment, and in variations thereof, it is desirable to remove heparin from whole blood. Extracorporeal circulation of blood—required in many surgical and medical procedures—requires the use of systemic heparin to prevent coagulation. Heparin is a highly negatively charged compound. In almost all cases it is necessary to neutralize or remove the heparin in the patient's blood prior to the completion of the surgical procedure. This is required to prevent post-operative bleeding complications. The most commonly used means for neutralizing heparin in this situation is by treatment with protamine sulfate. Unfortunately, the administration of protamine sulfate has several adverse side affects.

Other efforts to remove heparin from whole blood have been investigated. For example, U.S. Pat. No. 4,373,023 of Langer describes a support on which heparinase has been immobilized, an enzyme that degrades heparin. Others have attempted to use supported or immobilized protamine for heparin removal. See U.S. Pat. No. 4,800,016 of Yang; and Hou et al., *Art Organs.*, 14:436-442, 1990.

Affinity or ion exchange chromatography allows purification or separation of most chemicals based on the molecules biological function or chemical structure. The separation process occurs because of variations in affinity between the individual members of a mixture of components to a ligand or reactive group which is immobilized on an insoluble support or substrate. The substrates used in affinity chromatography generally are openly porous, have large surface areas, and contain some functionality that can be easily modified for the introduction of ligands. See, for example, Dean & Johnson, *Affinity Chromatography: a Practical Approach*, IRL Press, Oxford, 1985. The support materials preferably are strong, relatively heat insensitive, and preferably do not grow or "swell" significantly when in solution.

A common substrate or support is agarose beads, which possess a high degree of surface hydroxyl groups (—OH). The hydroxyl group is ideal for support materials due to its ability to be easily converted to other reactive functionalities such as aldehydes, or to be directly reacted with desired ligands. Ion exchange materials configured as flat, flexible sheets have found widespread use as support materials due to their physical characteristics and ease of use. See, for example, U.S. Pat. No. 4,663,163 of Hou. The sheet supports are commercially available with a variety of reactive groups such as an aldehyde functionality. The ion exchange materials of the present invention are prepared by the simultaneous or serial treatment of a support material with chemicals that place both quaternary ammonium functionalities and polyethylene oxide units on the surface of the support. The anion exchange materials as disclosed herein are capable of retaining their anion exchange capabilities while also being biocompatible with the components of whole blood. In a preferred embodiment, the anion ion exchange material is used to remove heparin from whole blood.

Efforts to make affinity or chromatographic materials biocompatible have been made in the past. The use of polyethylene oxide moieties on the surface of the materials to increase biocompatibility to surfaces for certain purposes has been described. See, U.S. Pat. No. 4,424,311 of Nagoaka et al; and U.S. Pat. No. 4,678,468 of Hiroyoshi. It has been shown that the ability to confer biocompatibility is proportional to the chain length of the polymer units attached to the surface of the support. See, e.g., Mori et al., *Trans Am Soc Artif Inter Organs*, 28:459–463, 1982; Andvade et al., *Trans Am Soc Artif Intern Organs*, 33:75–84, 1987.

Other researches have used quaternary ammonium chemicals to ionically bind an antithrombic agent to a surface. In U.S. Pat. No. 4,678,660 of McGary, et al., heparin was complexed with the quaternary compound tridodecyl methyl ammonium chloride and incorporated into polyurethane. In U.S. Pat. No. 4,690,973 of Noishiki et al., glycidyl trimethyl ammonium chloride (GTMAC) was reacted with collagen, and heparin was immobilized on the surface.

Despite the desirability of obtaining biocompatible anion exchange materials, the prior art does not describe any attempt to include immobilized cationic species and polyethylene oxides in such a way to obtain the materials disclosed herein.

In a further reference, a heparin/hydrogel coating was described as a method of improving the biocompatability of activated carbon for hemoperfusion. See, U.S. Pat. No. 4,048,064 of Clark. Macroreticular resin material or coated activated charcoal may also be used in the disclosed process and produce biocompatible hemoperfusion materials.

SUMMARY OF THE INVENTION

The present invention includes the novel use of a known material as a chromatographic support. The sheet material is comprised of a heat entangled blend of polyester (45%) and cellulose (55%) fibers. Also included is a method for the production of a biocompatible anion exchange material that is prepared by the treatment of a hydroxylated chromatographic support material with a mixture of reagents in order to react the hydroxyl groups on said support with the reagents to covalently bind quaternary ammonium units and long chain polymeric units on the surface of the support.

The anion exchange materials prepared by such method are also included within the scope of this invention. Such materials are comprised of a chromatographic support with covalently bound quaternary ammonium units and long chain polymer units.

In a preferred embodiment, the chromatographic support is a sheet of a heat entangled blend of polyester and cellulose, that is reacted with a blend of glycidyl trimethyl ammonium chloride (GTMAC) and bis glycidyl polyethylene oxide (GPEO).

Further included in the present invention is a method for selectively removing anionic species from solution by passing the solution in contact with the biocompatible anion exchange materials of the present invention. In a preferred embodiment, the anionic species is heparin and the solution is whole blood. A method for treating patients is also disclosed wherein a patient is treated with a medical agent (e.g., heparin) and at some point in time the medical agent is removed from the patient by extracorporeally passing a body fluid of the patient in contact with the biocompatible anion exchange material of the present invention. And finally, methods for treating blood extracorporeally are described wherein the extracorporeal process includes the introduction of heparin into the blood, and—before reintroduction of the blood into the patient—passing the blood in contact with the biocompatible anion exchange material to remove the heparin.

DETAILED DESCRIPTION OF THE PREFERRED EMBODIMENTS

Figure 1:
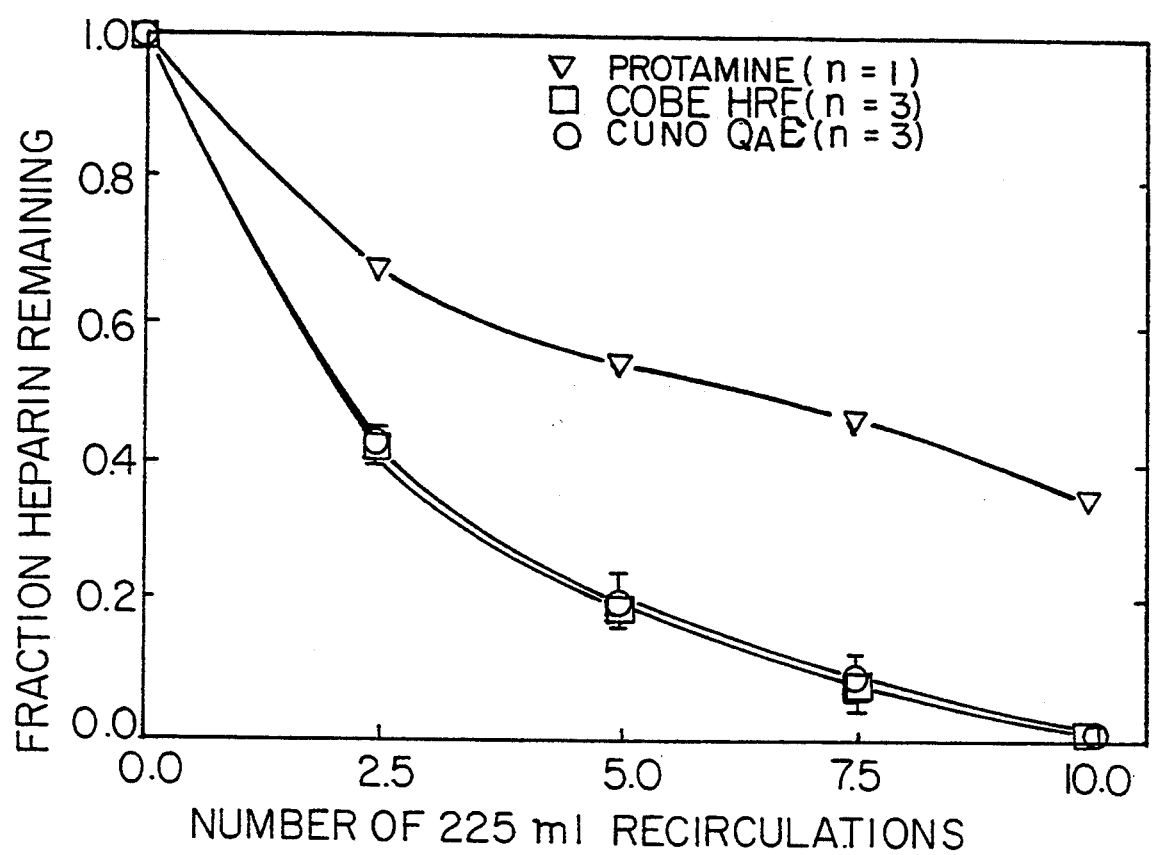
FIG. 1 is a graph that depicts the in vitro removal of heparin from bovine blood. The graph plots the fraction of heparin remaining in the blood sample versus the number of times the total volume of blood was circulated in contact with a given chromatographic material. Results are shown for a supported protamine (▽), the biocompatible anion exchange material of the present invention (□), and a commercially available anion exchange material known as Cuno QAE (o).

This invention describes a novel biocompatible anion exchange material. Anion exchange materials are used in a variety of purification or separation procedures. In some cases such materials can be used in batch reactions, but they are more typically used in flow or chromatographic procedures. Given compounds in a solution may be separated or purified based on the relative affinities of materials in a mixture to the reactive group on the surface of the anion exchange material. Anion exchange materials are a subspecies of a general class of affinity chromatographic materials.

The anion exchange materials of the present invention are comprised of a carrier support which has been treated with a plurality of reagents so that the surface of the support contains ion exchange elements and biocompatibility elements.

The carrier support may be comprised of any of the widely known and commercially available support materials commonly used by those skilled in the art. Carrier supports are typically highly porous, have a relatively large surface area, and have reactive functionalities. Detailed descriptions of the history of the development of carrier supports and the commonly used methods for converting carrier supports into affinity materials are described in U.S. Pat. No. 4,663,163 of Hou, and Dean, Johnson & Middle (eds.): *A Practical Approach*, IRL Press, Oxford, 1985, both of which are incorporated herein by reference.

In a preferred embodiment of the invention, the carrier support is comprised of a sheet of heat entangled blend of polyester (45%) and cellulose (55%) fibers.

The nonwoven blend has a hydroentangled construction that is made without chemical binders or additions, has a basis weight of about 66 g/m², and tensile strength of 15.9 kg. in the machine direction and 9.1 kg. in the cross direction. Such material can be obtained from The Texwipe Company (of Upper Saddle River, N.J.) as a clean room wiper sold under the trademark of "TECHNICLOTH". This sheet material has superior dry and wet strength relative to commercially available sheet support materials.

As with all carrier support methods, the TECHNICLOTH material has surface hydroxyl (—OH) groups that allow for the attachment of desired functional groups to the surface of the support. For example, the hydroxyl groups may be reacted with glycidyl groups, carboxylic acid or carboxylic acid derivatives. Alternatively, the surface hydroxyl groups may be derivitized prior to functionalization. In one embodiment, the hydroxyl groups are reduced to aldehydes according to procedures well known in the art, and the aldehydes are reacted with the primary amines of proteins to form covalently bound protein chromatographic materials. The hydroxyl groups on the surface of the TECHNICLOTH are not unique from those found in most carrier support materials, and the vast body of knowledge for derivitizing supports would be well known to those skilled in the art.

In a preferred embodiment of this invention, anion exchange materials are prepared by reacting carrier support materials simultaneously with a plurality of chemicals species that will react with the hydroxyl groups of the support. A first chemical species will incorporate ion exchange capability on the surface of the support, and a second chemical species will convey biocompatibility to the support. In a preferred embodiment, the ion exchange capability is created by the use of quaternary ammonium groups and the preferred first chemical species is glycidyl trimethyl ammonium chloride (GTMAC). In a preferred embodiment, the biocompatibility is created by using polyethylene oxide units, and the preferred second chemical is bis glycidyl polyethylene oxide (GPEO).

It is to be understood that other chemicals could be used to effect the same or substantially similar results, and that such chemicals would be known or readily apparent to those of ordinary skill in the art. The only requirement is that the selected chemicals be capable of reacting with the reactive sites of the chosen support material.

In a preferred embodiment, the given support material is immersed in an aqueous solution containing from 5 to 60 weight percent GTMAC and 0.1 to 10 weight percent GPEO for from 0.5 to 24 hours. In a preferred embodiment, the GTMAC utilized is a 70% aqueous solution, and the GPEO is a solid material. The reaction may be catalyzed by the addition of a base such as NaOH. GPEO to be used in this invention contains greater than 10 and less than 200 repeating ethylene oxide units. In a preferred embodiment, the GPEO contains greater than 25 and less than 100 repeating units, and in the preferred embodiment, the GPEO contains about 70–80 repeating units and has a molecular weight of about 3,300.

The weight ratio of GTMAC to GPEO in the solution used to create the anion exchange materials of the present invention is between about 50 to 200. In the preferred embodiment, the weight ratio of GTMAC to GPEO is about 80. It can be roughly assumed that the surface of the anion exchange material contains a ratio of ammonium salt units to polyethylene oxide units roughly equivalent to the ratio used in the solution.

In the preferred embodiment, bis glycidyl polyethyle oxide is used, and it may be assumed that in at least some cases both glycidyl functionalities will react with the surface of the support to form "looped" species. It is believed, however, that mono-reactive polyethylene oxide units that can not form such species would be equally effective in conveying biocompatability to the surface of the support.

In one embodiment of the present invention, the anion exchange materials of the present invention are utilized to remove anionic species from bodily fluids. Particularly useful is the removal of anionic species from whole blood. Such species include heparin, bilirubin, barbiturates, and any other anionic species—endogenous or exogenous—that may be found naturally in the blood or that has been introduced into the blood either as part of a medical treatment or as a mood altering drug. In the preferred embodiment, the bodily fluid is passed, extracorporeally, in contact with the anion exchange material. However, the present invention also includes the use of anion exchange material in a device such that bodily fluids are passed in contact with the material intracorporeally.

The removal of anionic species from bodily fluids may be part of a medical treatment as described in co-pending U.S. patent application Ser. No. 07/562,009, specifically incorporated herein by this reference. According to this method, a medical agent is administered to a patient and following a given period of time, the agent is removed from the patient's system by extracorporeally passing a body fluid of the patient in contact with the anion exchange material to specifically remove the agent. In one embodiment of this method, the medical agent is heparin—administered to prevent blood clotting during certain surgical procedures—and the extracorporeal treatment occurs following surgery.

In a variant embodiment of this method, both the treatment of the bodily fluid with an anionic medical agent and the removal of the agent with the anionic exchange material are extracorporeal. For example, blood may be removed from a patient for dialysis or plasma exchange, and it may be desirable to add heparin to the blood before it enters the processing equipment, and removed from the blood before it reenters the patient.

The present invention also includes the use of heparin introduction and removable modules associated with extracorporeal blood processing equipment. The heparin introduction module may consist of any automated or manual fluid metering devices such as are familiar with those skilled in the art. The heparin removal modules would consist of means for passing the processed blood in contact with the anion exchange materials of the present invention. Means for passing fluids in contact with sheet ion exchange materials are also well known in the prior art. Blood processing includes plasma exchange, dialysis, and oxygenation, and other well known blood processing equipment where it is advantageous to add heparin to the blood prior to processing.

Although in the preferred embodiment the anion exchange materials are utilized in the removal of anionic material from whole blood, the materials may also be used to remove such material from other bodily fluids—e.g., plasma, peritoneal fluids—as well as from aqueous or organic based solvent streams.

The above descriptions of this invention can be better understood when read in conjunction with the Examples presented below. It should be understood, however, that the present invention must not be limited to the specifics of such Examples.

EXAMPLES

In one example, the disclosed process is used to make an anionic exchange material from a flat sheet of TECHNICLOTH. The utility of the material is then demonstrated with the in vitro removal of heparin from bovine blood. Heparin removal with the TECHNICLOTH reacted with GTMAC and GPEO (hereafter referred to as TECH-GG) is compared with protamine sulfate also immobilized on TECHNICLOTH using the procedure recommended by Yang (U.S. Pat. No. 4,800,016) and with the anion exchange paper available from Cuno, Inc. (Cuno QAE). The biocompatibility is evaluated from the amount of platelets removed from bovine blood with each of these materials. The following sections describe the materials used, the reaction of GTMAC and GPEO with the TECHNICLOTH, the heparin removal experimental protocol, and the results.

Materials

The glycidyl trimethyl ammonium chloride (GTMAC) was obtained from the Degussa Corporation of Ridgefield Park, N.J. as QUAB-151, a 70% aqueous solution. The bis glycidyl polyethylene oxide was obtained in solid form (Cat. #P2672, polyoxyethylene, bis glycidyl) from Sigma Chemical in St. Louis, Mo. Sodium hydroxide (NaOH) was used to catalyze the reaction and was obtained from Curtin Matheson Scientific (CMS) in Aurora, Colo. Sodium chloride (NaCl), dibasic sodium phosphate, and monobasic sodium phosphate were used to prepare buffers and were also obtained from CMS. The bovine blood was collected from donor cows the morning of use, and was provided by Hemo Lab of Broomfield, Colo. Beef lung heparin was obtained from Organon Inc. of West Orange, N.J. in 1000 USP units/ml ampules.

Example 1: Preparation of Anion Exchange Materials

Five, 5×20 cm sheets of TECHNICLOTH were immersed in a 0.3M NaOH aqueous solution containing 40 g% GTMAC and 0.5 g% GPEO for 24 hours. This was done by first dissolving 5 gms of GPEO and 12.96 gms of NaOH in 360 ml water in a 1100 ml jar. The TECHNICLOTH sheets were then added and the contents swirled. Immediately, 610 gms of liquid QUAB-151 (GTMAC) were added, followed by water to a total volume of 1080 mls. The contents were mixed and the jar was let set for 24 hours with no further agitation.

At the end of the 24 hours the substrate sheets were removed and washed with copious amounts of water, then rinsed with six 1000 ml batches of equilibration buffer (0.1M sodium phosphate, 0.5M NaCl, pH 8.0) and left at 4° C. overnight in the same. The equilibration buffer was then replaced with PBS (phosphate buffered saline: 0.01M sodium phosphate, 0.84 g% NaCl, pH 7.4) and the substrate sheets stored at room temperature until their use in the heparin removal experiments.

Example 2: Heparin Removal Experimental Protocol

A test heparin removal filter (HRF) is constructed by sandwiching one 5×20 cm sheet of a candidate material between two sheets of polypropylene netting. The three sheets are then placed in a fixed channel device through which blood can be pumped. This device, constructed of polycarbonate, holds the filter material in place so that blood can be passed with equal velocity on both sides. The depth of the 5 cm wide flow path can be varied by the use of stainless steel shims. By using a thicker shim for a thicker candidate material, the depth of the flow path can be held constant. The purpose of the netting is to separate the filter material from the housing wall to create equal flow paths. Blood enters the bottom of the housing, is split by the filter material, and flows vertically (along the 20 cm dimension).

Example 3: Comparison Results

For the technicloth-protamine sulfate reaction the procedure of Yang was followed with activation by cyanogen bromide at a concentration of 0.1 g/ml and exposure time of 5 minutes. In the immobilization step, the protamine concentration was 10 mg/ml with overnight exposure. The Cuno material was used as recommended by Cuno Inc.

In order to test the heparin removal efficiency and blood cell compatibility of the TECH-GG and demonstrate the disclosed process, an experimental protocol was designed to simulate the envisioned use of a heparin filter. A reservoir of bovine blood containing 8 units/ml of beef lung heparin was circulated through the fixed channel device. The reservoir volume was chosen so that the total system volume (prime of the housing with PBS included) was 225 mls. The reservoir was pumped at 150 ml/min and blood samples taken at timed intervals. The blood samples were analyzed for heparin by the Azure A method (U.S. Pat. No. 4,678,660 of McGary) and eleven hematological parameters were evaluated with a Coulter Counter Model S-Plus IV, of which the most sensitive indicator of blood trauma was the platelet count. After the total volume of 225 mls had been circulated through the filter 10 times (15 minutes) the experiment was terminated. Multiple passes through the filter insured that "activated" platelets will have been removed.

The heparin removal efficiency of the TECH-GG was compared to the Cuno-QAE material and immobilized protamine, and the results are shown in FIG. 1. The "fraction of heparin remaining", or the amount of heparin remaining in the reservoir over the initial amount (corrected for dilution) is plotted versus the number of reservoir recirculations (225 ml) for each of these materials in FIG. 1.

Figure 2:
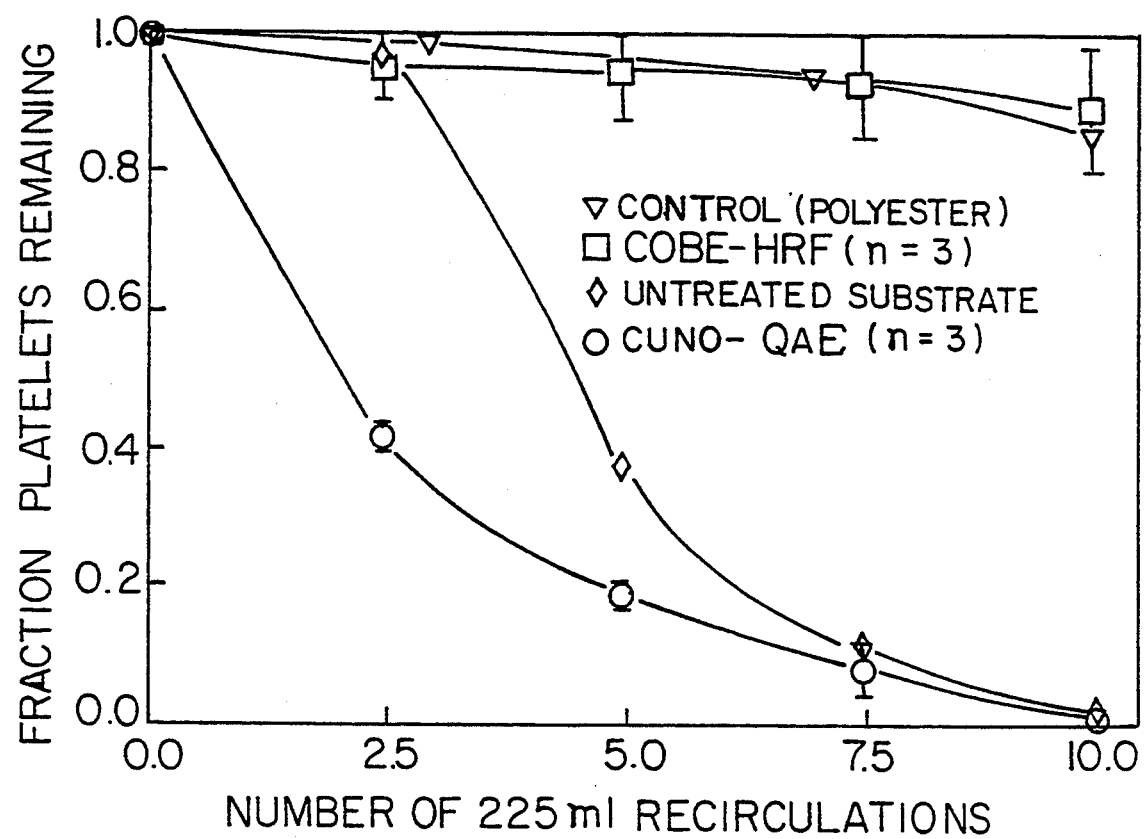
FIG. 2 is a graph showing the in vitro platelet removal from bovine blood. The graph plots the fraction of platelets remaining in the blood sample versus the number of times the total volume of blood was circulated in contact with a given chromatographic material. Results are shown for a polyester control (□), the biocompatible anion exchange material of the present invention (▽), the chromatographic support material of the present invention (***), and a commercially available anion exchange material known as Cuno QAE (o).

In FIG. 2, the same experimental protocol described above was used to determine the amount of platelets removed from the bovine blood following repeated passes through the sample containing reservoir.

The results of FIGS. 1 and 2 show that the anion exchange materials of the present invention are effective in heparin removal, while retaining excellent biocompatibility—as evidenced by its not significantly depleting the blood of platelets.

We claim:

1. A biocompatible anion exchange material comprised of:
   polyester;
   cellulose comprising a plurality of hydroxyl groups,
      said cellulose and polyester forming a heat entangled nonwoven blend;

quaternary ammonium functionalities covalently attached to said cellulose at at least some of said hydroxyl groups; and polyethylene oxide covalently attached to said cellulose at at least some of said hydroxyl groups.

2. A method for preparing biocompatible anion exchange materials comprising:

placing a support comprised of surface hydroxyl groups in a solution containing GPEO and GTMAC; and drying the support material.

3. A method for removing anionic species from a bodily fluid comprising:

contacting said bodily fluid with an anionic exchange material, wherein said material is comprised of a heat entangled nonwoven blend of polyester and cellulose, having quaternary ammonium functionalities covalently attached to said cellulose and polyethylene oxide functionalities covalently attached to said cellulose.

4. The biocompatible anion exchange material of claim 1 wherein the weight ratio of quaternary ammonium functionalities to polyethylene oxide functionalities is 50–200.

5. The biocompatible anion exchange material of claim 1 wherein said cellulose polyester composite is comprised of 45% polyester and 55% cellulose.

6. The biocompatible anion exchange material of claim 1 wherein said cellulose polyester composite has a tensile strength of greater than 9.0 kg.

7. A biocompatible anion exchange material prepared according to the method of claim 2 comprising:

placing a support comprised of a heat entangled nonwoven blend of polyester and cellulose fibers having surface hydroxyl groups, in a solution containing GPEO and GTMAC; and drying the support.

8. The method of claim 2 wherein said GTMAC and GPEO are in a weight ratio of 50–200.

9. The method of claim 2 wherein said blend is comprised of 45% polyester and 55% cellulose fibers.

10. The method of claim 2 wherein said solution contains NaOH.

11. The method of claim 2 wherein said support is in contact with said solution for at least 24 hours.

12. The method of claim 3 wherein said bodily fluid is whole blood.

13. The method of claim 3 wherein said anionic species is heparin.

14. The method of claim 3 wherein said heat entangled nonwoven blend is comprised of 45% polyester and 55% cellulose fibers.

15. The method of claim 3 wherein said anionic exchange material is prepared according to the method comprising:

placing the heat entangle nonwoven blend of polyester and cellulose comprised of surface hydroxyl groups in a solution containing GPEO and GTMAC; and drying the support.

16. A method for preparing biocompatible anion exchange materials comprising:

placing a heat entangled nonwoven blend comprised of polyester and cellulose in a solution containing GPEO and GTMAC capable of covalently attaching polyethylene oxide and quaternary ammonium functionalities to said cellulose; and drying the support.

17. A method for preparing biocompatible anion exchange materials of claim 1 comprising:

placing a support comprised of surface hydroxyl groups in a solution containing GPEO and GTMAC, wherein said support is a composite comprised of a heat entangled nonwoven blend of 45% polyester and 55% cellulose fibers; and drying the support material.

18. The method of claim 17 wherein said solution contains NAOH.

19. The method of claim 17 wherein said support is in contact with said solution for at least 24 hours.

20. A method for removing anionic species from a bodily fluid comprising:

contacting said bodily fluid with an anionic exchange material, wherein said material is comprised of a composite polyester and cellulose heat entangled nonwoven blend having quaternary ammonium functionalities covalently attached to said cellulose and polyethylene oxide functionalities covalently attached to said cellulose, said quaternary ammonium functionalities and polyethylene oxide functionalities formed by placing said composite support material having surface hydroxyl groups in a solution containing GPEO and GTMAC, and drying said support.

21. The method of claim 20 wherein said bodily fluid is whole blood.

22. The method of claim 20 wherein said anionic species is heparin.

23. The biocompatible anion exchange material prepared according to claim 2.

24. The biocompatible anion exchange material prepared according to claim 16.

25. The biocompatible anion exchange material prepared according to claim 17.

* * * * *

UNITED STATES PATENT AND TRADEMARK OFFICE
CERTIFICATE OF CORRECTION

PATENT NO. : 5,354,472
DATED : October 11, 1994
INVENTOR(S) : Ben Brian, III., Marc Voorhees, Lloyd Forrestal It is certified that error appears in the above-indentified patent and that said Letters Patent is hereby corrected as shown below:

Title Page, Block [19] below "United States Patent":
   "Voorhees et al." should be --Brian et al.--.

Title Page, Block [75] Inventors: "Marc Voorhees, Arvada; Ben F. Brian, III, Littleton; Lloyd Forrestal, Boulder, all of Colo." should be --Ben F. Brian, III, Littleton; Marc Voorhees, Arvada; Lloyd Forrestal, Boulder; all of Colo.--.

Column 6, lines 17-18, insert --either-- before "endogenous".

Column 7, line 33 "Mo." should be --MO.--.

Signed and Sealed this

Twenty-fourth Day of October, 1995

Attest:

BRUCE LEHMAN

Attesting Officer

Commissioner of Patents and Trademarks